United States Patent
Abbasi et al.

(10) Patent No.: US 11,737,888 B1
(45) Date of Patent: Aug. 29, 2023

(54) SPINAL FUSION IMPLANT SYSTEM AND METHOD

(71) Applicant: Advance Research System, LLC, Edina, MN (US)

(72) Inventors: Hamid R. Abbasi, Edina, MN (US); Kenneth R. Barra, Dallas, GA (US)

(73) Assignee: Advance Research System, LLC, Edina, MN (US)

( * ) Notice: Subject to any disclaimer, the term of this patent is extended or adjusted under 35 U.S.C. 154(b) by 163 days.

(21) Appl. No.: 17/027,164

(22) Filed: Sep. 21, 2020

Related U.S. Application Data (60) Provisional application No. 62/902,506, filed on Sep. 19, 2019.

(51) Int. Cl.
*A61F 2/44* (2006.01)
*A61F 2/46* (2006.01)

(52) U.S. Cl.
CPC ............ *A61F 2/447* (2013.01); *A61F 2/4611* (2013.01); *A61F 2002/4629* (2013.01)

(58) Field of Classification Search
CPC .................... A61F 2/447; A61F 2/4611; A61F 2002/4629
See application file for complete search history.

(56) References Cited

U.S. PATENT DOCUMENTS

| | | |
|---|---|---|
| 6,443,987 B1 | 9/2002 | Bryan |
| 6,942,698 B1 | 9/2005 | Jackson |
| 7,105,023 B2 | 9/2006 | Eckman |
| 7,175,667 B2 | 2/2007 | Saunders et al. |
| D552,734 S | 10/2007 | Eckman |
| 7,534,267 B2 | 5/2009 | Eckman |
| 7,674,295 B2 | 3/2010 | Eckman |
| D619,719 S | 7/2010 | Pannu |
| D620,110 S | 7/2010 | Courtney et al. |
| D620,112 S | 7/2010 | Courtney et al. |

(Continued)

FOREIGN PATENT DOCUMENTS

| | | |
|---|---|---|
| EP | 1099429 A1 | 5/2001 |
| FR | 2946245 | 12/2010 |

(Continued)

OTHER PUBLICATIONS

Design World "Peek thermoplastic used to develop spinal spacer devices" (Nov. 29, 2012) downloaded from internet at http://www.designworldonline.com/peek-thermoplastic-used-to-develop-spinal-spacer-devices/.

(Continued)

*Primary Examiner* — Nicholas J Plionis
(74) *Attorney, Agent, or Firm* — Christensen, Fonder, Dardi & Herbert PLLC; Stuart J. Olstad (57) ABSTRACT

A spinal implant system includes an inserter that passes through a spinal implant for attachment to a distal end of the spinal implant. By this arrangement, stability of the implant system is enhanced for placement of the spinal implant while reducing local stresses imparted at the attachment. The disclosed spinal implant system may include an access tube that is coupled to a proximal end of the spinal implant. After placement of the spinal implant, the inserter may be removed from the spinal implant and access tube, providing access via the access tube to an interior of the spinal implant and the corresponding space between the vertebral endplates.

19 Claims, 9 Drawing Sheets

(56) References Cited

U.S. PATENT DOCUMENTS

| | | |
|---|---|---|
| D620,113 S | 7/2010 | Courtney et al. |
| D627,468 S | 11/2010 | Richter et al. |
| 7,850,734 B2 | 12/2010 | Oh et al. |
| D630,749 S | 1/2011 | Tornier |
| 7,867,277 B1 | 1/2011 | Tohmeh |
| 7,938,857 B2 | 5/2011 | Garcia-Bengochea et al. |
| 8,002,831 B2 | 8/2011 | Burd et al. |
| 8,025,697 B2 | 9/2011 | McClellan, III et al. |
| 8,062,374 B2 | 11/2011 | Markworth et al. |
| D653,757 S | 2/2012 | Binder |
| 8,137,402 B2 | 3/2012 | Eckman |
| 8,147,554 B2 | 4/2012 | Hansell et al. |
| 8,167,886 B2 | 5/2012 | Eckman |
| D665,081 S | 8/2012 | Hansell et al. |
| 8,273,128 B2 | 9/2012 | Oh et al. |
| D675,736 S | 2/2013 | Garza-Vale et al. |
| 8,414,654 B1 | 4/2013 | Ganey |
| 8,425,610 B2 | 4/2013 | Guyer et al. |
| 8,496,709 B2 | 7/2013 | Schell et al. |
| 8,535,378 B2 | 9/2013 | Jackson |
| 8,568,416 B2 | 10/2013 | Schmitz et al. |
| 8,591,589 B2 | 11/2013 | McCombe et al. |
| 8,613,745 B2 | 12/2013 | Bleich |
| 8,617,163 B2 | 12/2013 | Bleich |
| 8,663,331 B2 | 3/2014 | McClellan, III et al. |
| 8,679,189 B1 | 3/2014 | Ganey et al. |
| 8,685,096 B2 | 4/2014 | Davenport |
| 8,709,087 B2 | 4/2014 | Cragg |
| 8,747,473 B2 | 6/2014 | Burd et al. |
| 8,845,727 B2 | 9/2014 | Gottlieb et al. |
| 8,864,839 B2 | 10/2014 | Ganey |
| 8,870,957 B2 | 10/2014 | Vraney et al. |
| D718,860 S | 12/2014 | Farris et al. |
| 8,900,310 B2 | 12/2014 | Carlson et al. |
| D722,695 S | 2/2015 | Kaufmann et al. |
| 8,979,927 B2 | 3/2015 | Huntsman et al. |
| 8,992,622 B2 | 3/2015 | Ullrich, Jr. et al. |
| 9,015,922 B2 | 4/2015 | Ganey |
| D731,063 S | 6/2015 | VerHage et al. |
| D732,667 S | 6/2015 | McCormack et al. |
| D733,303 S | 6/2015 | Peterson et al. |
| D737,446 S | 8/2015 | Butler et al. |
| 9,107,768 B2 | 8/2015 | Schell et al. |
| 9,138,330 B2 | 9/2015 | Hansell et al. |
| D741,488 S | 10/2015 | Tohmeh et al. |
| D745,156 S | 12/2015 | McCormack et al. |
| 9,198,774 B2 | 12/2015 | Pisharodi |
| 9,226,835 B2 | 1/2016 | Schell et al. |
| D750,249 S | 2/2016 | Grimberg, Jr. et al. |
| 9,265,622 B2 | 2/2016 | Schell et al. |
| 9,289,312 B2 | 3/2016 | Davenport et al. |
| 9,295,562 B2 | 3/2016 | Lechmann et al. |
| D753,305 S | 4/2016 | Butler |
| 9,320,610 B2 | 4/2016 | Alheidt et al. |
| 9,320,618 B2 | 4/2016 | Schmitz et al. |
| 9,364,344 B2 | 6/2016 | Whipple |
| 9,381,049 B2 | 7/2016 | McCormack et al. |
| 9,445,914 B2 | 9/2016 | Milz et al. |
| 9,445,918 B1 * | 9/2016 | Lin .................. A61F 2/4684 |
| 9,566,170 B2 | 2/2017 | Schell et al. |
| 2001/0020185 A1 * | 9/2001 | Ray .................. A61F 2/4611 |
| | | 623/17.11 |
| 2002/0169508 A1 | 11/2002 | Songer et al. |
| 2003/0023306 A1 | 1/2003 | Liu et al. |
| 2003/0105528 A1 | 6/2003 | Shimp et al. |
| 2003/0139812 A1 | 7/2003 | Garcia et al. |
| 2006/0167548 A1 | 7/2006 | Jackson |
| 2008/0154377 A1 * | 6/2008 | Voellmicke .......... A61F 2/4611 |
| | | 623/17.16 |
| 2011/0144755 A1 | 6/2011 | Baynham et al. |
| 2012/0065613 A1 | 3/2012 | Pepper et al. |
| 2014/0100657 A1 | 4/2014 | McCormack et al. |
| 2015/0005881 A1 | 1/2015 | Connor et al. |
| 2015/0100129 A1 | 4/2015 | Waugh et al. |
| 2015/0173917 A1 | 6/2015 | Radcliffe et al. |
| 2016/0030188 A1 | 2/2016 | Lynn et al. |
| 2016/0081814 A1 | 3/2016 | Baynham |
| 2016/0113773 A1 | 4/2016 | Ganem |

FOREIGN PATENT DOCUMENTS

| | | |
|---|---|---|
| JP | 1607071 | 6/2018 |
| KR | 30-0543254 | 4/2010 |
| WO | WO2013/009462 A2 | 1/2013 |
| WO | WO-2018112324 A2 * | 6/2018 ........... A61F 2/4455 |

OTHER PUBLICATIONS

Nexxt Spine "Honour tPLIF Spacer System" downloaded from the internet at http://www.nexxtspine.com/products/honour-tplif-spacer-system, published prior to Feb. 13, 2017.

Next Spine "Honour tPLIF Spacer System" downloaded from the internet on Oct. 20, 2017 at http://www.nexxtsgine.com/gallery/honour_tplif/new/169.

Next Spine "Honour TLIF Spacer System" downloaded from the internet on Oct. 20, 2017 at http://www.nexxtsgine.com/products/Honour-TLIF-Spacer-System.

Next Spine "Honour Allo-C Allograft System" downloaded from the internet on Oct. 20, 2017 at http://www.nexxtspine.com/products/honour-allo-c-allgraft-system.

International Search Report for Application No. PCT/US2017/066641 dated Jun. 25, 2018 (6 pages).

Next Spine "Honour Orb Cervical Spacer System" downloaded from the internet on Oct. 20, 2017 at http://www.nexxtspine.com/products/honour-orb-cervical-spacer-system.

* cited by examiner

SPINAL FUSION IMPLANT SYSTEM AND METHOD

RELATED APPLICATIONS

This application claims the benefit of U.S. Provisional Patent application No. 62/902,506, filed Sep. 19, 2019, the disclosure of which is incorporated by reference herein in its entirety.

FIELD OF THE DISCLOSURE

The disclosure relates generally to spinal fusion apparatuses and methods, and more specifically to spinal implants and systems for their placement.

BACKGROUND

Spinal implants are utilized for spinal fusion (arthrodesis) to restrict movement between vertebrae. The implants support and immobilize adjacent vertebrae while new bone tissue grow between the vertebrae.

Surgically implanting the spinal implants requires placement of the implant at desired locations and orientations, and in some procedures require substantial manipulation forces (thrust and torque) to accomplish insertion of the implant. Many spinal implants include a cage through which the new bone tissue can grow with a nose portion that aids in the insertion. However, the stresses generated on the spinal implants during implantation can be substantial, which can dictate the thickness of the cage members and the subsequent size of the interior chamber of the cage.

A spinal implant and implant system that facilitates manipulation of the implant while reducing the stresses incurred by the cage during implantation would be welcomed.

SUMMARY OF THE DISCLOSURE

Various embodiments of the disclosed spinal implant system include an inserter that passes through a spinal implant for attachment to a distal end portion of the spinal implant. By this arrangement, the stability of the implant system is enhanced for placement of the spinal implant while reducing local stresses imparted at the attachment. Furthermore, the body portion of the spinal implant is not subject to the high compressive and torsional loads associated with the rigors of initially placing the spinal implant. Accordingly, the body portion may be configured to define a larger access port at the proximal end as well as a larger interior chamber without compromising the structural integrity of the implant. The larger access port and interior chamber can accommodate a broader range of cannulated instruments that may be used during the implantation process, such as rakes and endplate plungers, and also enable more ingrowth of tissue into and through the spinal implant.

Various embodiments of the disclosed spinal implant system include an access tube that is coupled to a proximal end of the spinal implant. After placement of the spinal implant, the inserter may be removed from the spinal implant and access tube, providing access to an interior of the spinal implant and the corresponding space between the vertebral endplates via the access tube.

Structurally, various embodiments of an implant for vertebral fusion are disclosed, comprising a body portion defining a central axis that extends from a proximal end portion through a distal end portion of the body portion, the body portion defining an access port at the proximal end portion and a mounting port at the distal end portion. The mounting port is accessible from a proximal face of the distal end portion. The access port is configured for passage of an inserter therethrough, the mounting port being configured for selective attachment to the inserter. In some embodiments, the proximal end portion and the distal end portion are separated by a pair of opposed side walls. The mounting port may be tapped for threaded engagement with the inserter. In some embodiments, the proximal face of the distal end portion includes a planar registration surface that surrounds the mounting port, the planar registration surface being substantially orthogonal to the central axis. The distal end portion may define a through-passage that passes therethrough for passage of a guide wire. In some embodiments, the body portion defines a superior opening and an inferior opening. The spinal implant may include a nose portion that extends in a distal direction from the distal end portion of the body portion. The nose portion may be concentric about the central axis. In some embodiments, the body portion, the access port, and the mounting port are concentric about the central axis. The central axis may be linear. In some embodiments, the access port is dimensioned for passage of a portion of the inserter having a maximum outer dimension in a range of 5 millimeters to 15 millimeters inclusive. In some embodiments, the access port is dimensioned for passage of a portion of the inserter having a maximum outer dimension in a range of 5 millimeters to 9 millimeters inclusive. In some embodiments, the access port is dimensioned for passage of a portion of the inserter having a maximum outer dimension in a range of 6 millimeters to 8 millimeters inclusive.

In various embodiments of the disclosure, a system for implanting a spinal implant is disclosed, comprising a spinal implant including a body portion defining a central axis that extends from a proximal end portion through a distal end portion of the body portion, the body portion defining an access port at the proximal end portion and a mounting port at the distal end portion, the mounting port being accessible from a proximal face of the distal end portion. An access tube may be configured for selective attachment to the access port of the spinal implant, and an inserter is configured to slide through the access tube and the access port and for selective attachment to the mounting port. In some embodiments of the disclosure, the inserter is an assembly that includes a shaft defining a central bore and a inner retainer translatable within the central bore. The inner retainer may include a threaded distal end for threadable connection with the mounting port. In some embodiments, the access port includes threads that mate with a threaded portion of the access tube for the selective attachment of the access tube to the access port. The threads of the access port may be female. In some embodiments, the mounting port includes female threads that mate with a distal end of the inserter for the selective attachment of the inserter to the mounting port. In some embodiments, the access port includes first threads that mate with a distal end of the access tube for the selective attachment of the access tube to the access port, and the mounting port includes second threads that mate with a distal end of the inserter for the selective attachment of the inserter to the mounting port. The inserter includes a distal face that may engage the distal end portion of the body portion when the inserter is selectively attached to the distal end of the spinal implant. In some embodiments, the proximal face of the distal end portion of the body portion includes a planar registration surface that surrounds the mounting port, the planar registration surface being orthogonal to the central axis and engaging the distal face of the inserter when the inserter is selectively attached to the distal end of the spinal implant.

In various embodiments of the disclosure, a method for implanting a spinal implant is disclosed, comprising: inserting an inserter through an access port defined at a proximal end portion of a spinal implant; and selectively attaching the inserter to a proximal face of a distal end portion of the spinal implant. The method may include attaching an access tube to the proximal end portion of the spinal implant, and inserting the inserter through the access tube. In some embodiments, the method comprises pounding a proximal end of the inserter to drive a shoulder of the inserter against the distal end portion of the spinal implant.

DETAILED DESCRIPTION OF THE DRAWINGS

Figure 1:
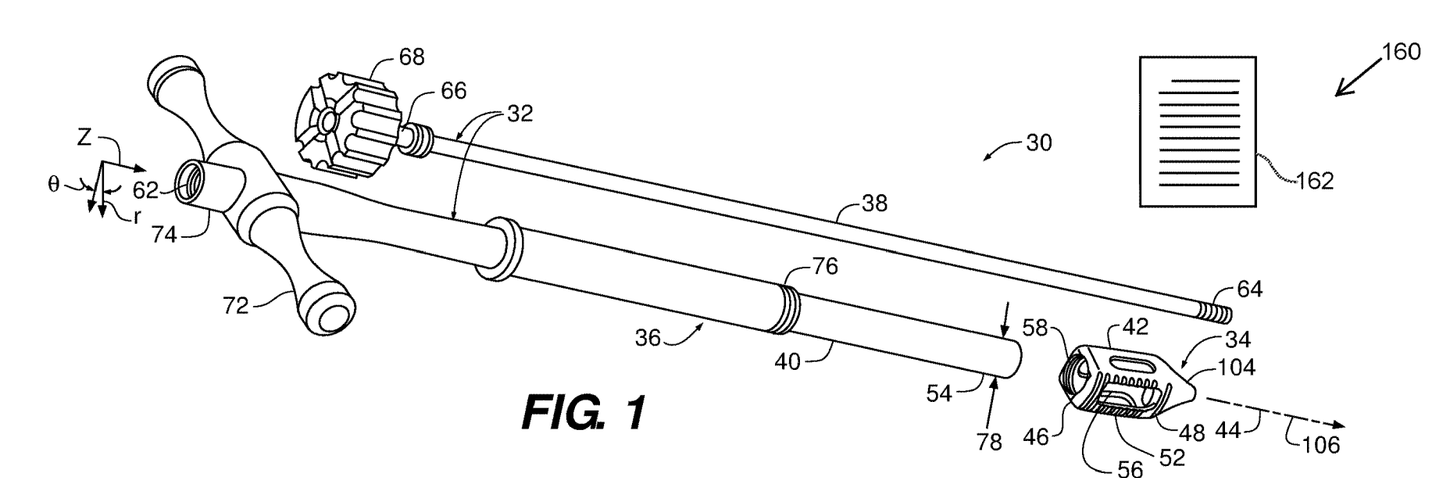
FIG. 1 is a perspective view of a partially assembled spinal implant system according to an embodiment of the disclosure.
Figure 2:
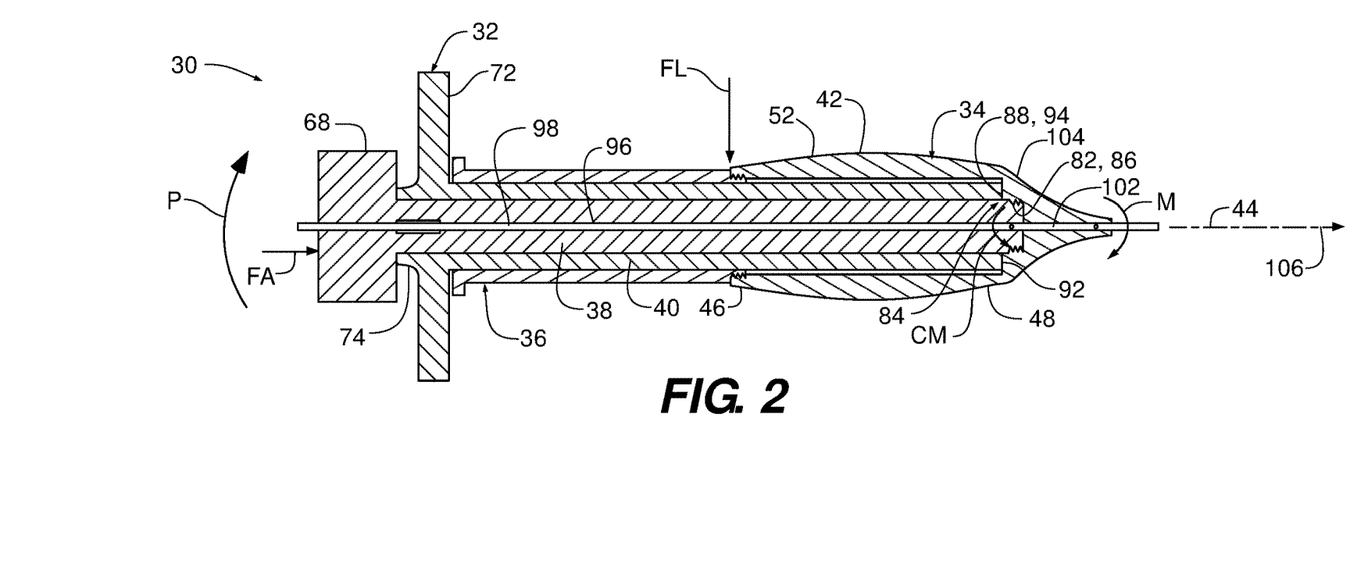
FIG. 2 is a sectional schematic of the spinal implant system of FIG. 1 according to an embodiment of the disclosure.

Referring to FIGS. 1 and 2, a spinal implant system 30 is depicted according to an embodiment of the disclosure. The spinal implant system 30 includes an inserter 32, a spinal implant 34, and, in some embodiments, an access tube 36. The inserter 32 includes a shaft 40 configured for insertion into the spinal implant 34. In some embodiments, the inserter 32 is an assembly that includes an inner retainer 38 translatable within the shaft 40.

The spinal implant 34 includes a body portion 42 defining a central axis 44 that extends from a proximal end portion 46 through a distal end portion 48 of the body portion 42. In some embodiments, the body portion 42 includes side walls 52 that separate the proximal and distal end portions 46, 48. A distal end portion 54 of the inserter 32 is selectively and directly attachable to the distal end portion 48 of the spinal implant 34. The body portion 42 may also define an interior chamber or receptacle 56 accessible via an access port 58 at the proximal end portion 46.

In some embodiments, the inserter 32 is an assembly that includes the shaft 40 configured to receive the inner retainer 38 that translates within a central bore 62 of the shaft 40. For embodiments utilizing the inner retainer 38, a distal end 64 the inner retainer 38 is configured to contact and mate directly to the distal end portion 48 of the body portion 42. In some embodiments, a tamping knob 68 may be attached to a proximal end 66 of the inner retainer 38. In some embodiments, a handle 72 is coupled to the proximal portion 74 of the shaft 40, for example, a T-handle (depicted). The access tube 36 is also selectively attachable to the spinal implant 34. The access tube 36 may include a distal portion 76 configured for the selective attachment. In some embodiments, the distal portion 76 of the access tube 36 is threaded (depicted).

The distal end portion 54 of the inserter 32 includes a maximum outer dimension 78 that extends orthogonal to the central bore 62 (i.e., parallel to the r direction of the r-O-z coordinate of FIG. 1). The access port 58 may be configured for passage of the distal end portion 54 of the inserter 32 therethrough. In some embodiments, the maximum outer dimension 78 of the distal end portion 54 is in a range of 5 millimeters to 15 millimeters inclusive. In some embodiments, the maximum outer dimension 78 of the distal end portion 54 is in a range of 5 millimeters to 9 millimeters inclusive. In some embodiments, the maximum outer dimension 78 of the distal end portion 54 is in a range of 6 millimeters to 8 millimeters inclusive. Herein, a range that is said to be "inclusive" includes the endpoint values of the stated range.

In assembly, the distal end portion 48 of the spinal implant 34 is mounted to the distal end portion 54 of the inserter 32 by sliding the proximal end portion 46 of the spinal implant 34 over the distal end portion 54 of the inserter 32. The distal end portion 54 of the inserter 32 thus passes through the access port 58 and the distal end portion 48 of the spinal implant 34 brought into engagement with the distal end portion 54 of the inserter 32 to form an attachment 82. A junction 84 is thereby formed between the inserter 32 and the spinal implant 34 which includes the attachment 82 (e.g., threaded connection) between the inserter 32 and a mounting port 86 as well as an interface 88 between a distal face 92 of the inserter 32 and a proximal face 94 of the distal end portion 48 of the spinal implant 34. In some embodiments, the access tube 36 is attached to the access port 58 of the spinal implant 34, for example by threaded engagement.

In operation, the spinal implant system 30, which may include the access tube 36, may be inserted into the patient by sliding a central passage 96 of the inserter 32 over a guide wire 98 leading to an implantation site. The operator may exert axial forces, rotational forces, and yaw/pitch forces on the spinal implant system 30, for example using the handle 72. The operator may also exert impact forces by pounding on the tamping knob 68, for example with the palm of a hand or with a mallet. In embodiments utilizing the inner retainer 38, the inserter 32 may be configured so that the tamping knob 68 engages the proximal portion 74 of the shaft 40 as the spinal implant 34 is seated against the distal face 92 of the distal end portion 54 of the shaft 40. This enables a significant portion of axial forces FA (FIG. 2) applied to the spinal implant system 30 may be transferred to the shaft 40, which is then transferred to the interface 88. The partial distribution of the axial forces FA to the interface 88 reduces stresses at the attachment 82. The guide wire 98 may be removed before the spinal implant 34 is driven into the implant site. Once the spinal implant 34 is in place, the inserter 32 is disconnected from the distal end portion 48 of the spinal implant 34 and removed from the spinal implant 34. For configurations utilizing the access tube 36, the inserter 32 is withdrawn from the access tube 36, leaving an access path to the interior of the spinal implant 34 via the access tube 36.

Functionally, inserting the distal end portion 54 of the shaft 40 through the proximal end portion 46 of the spinal implant 34 for connection to the distal end portion 48 of the spinal implant enhances the stability and rigidity of the spinal implant system 30 relative to conventional spinal implant systems. When a pitch force P (or yaw force) is applied to the inserter 32 to impart a moment M on the spinal implant 34 during the implantation process, a countering moment CM is generated at the junction 84 between the inserter 32 and a mounting port 86 (FIG. 2). In addition, deflections of the spinal implant system 30 can provide a reactionary lateral force FL at the access port 58 of the spinal implant 34 to partially counter the moment M and reduce the counter moment CM at the junction 84. In conventional implant systems that connect to a proximal end of a spinal implant, the countering of pitch and yaw moments is concentrated at a junction between the spinal implant and an inserter, which can create excessive stresses. These stresses are often accommodated by increasing the thickness of the body members, which can limit the size of the proximal access port and interior chamber. For the disclosed spinal implant system 30, the reactionary lateral force FL reduces the stresses generated at the junction 84, enabling the material thicknesses of the body portion to be reduced. Correspondingly, the internal dimensions of the interior chamber 56 may be increased.

Figure 5:
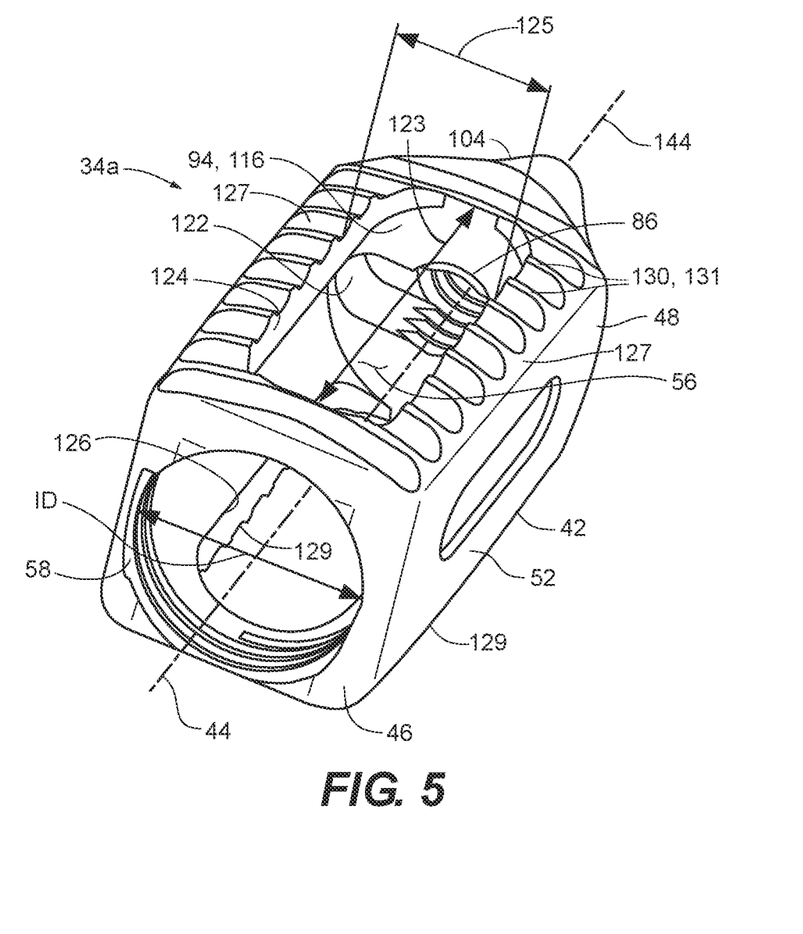
FIG. 5 is a perspective view of a spinal implant for use with the inserter of FIG. 4 according to an embodiment of the disclosure.

The access tube 36 and access port 58 may accommodate various cannulated instruments other than the inserter 32. Examples include rakes and scraping tools for treatment of the adjacent vertebral endplates of the subject spine, as well as cannulated end plungers, such as depicted and described at U.S. patent application Ser. No. 16/239,035 to Abbasi, filed Jan. 3, 2019, and U.S. patent application Ser. No. 16/839,167 to Abbasi et al., filed Apr. 3, 2020, both of which are owned by the owner of the present application. Such tools may operate, for example, through the superior and inferior openings 124 and 126 (FIG. 5)

The distal end portion 48 may define a through-passage 102 for passage of the guide wire 98. In some embodiments, the spinal implant 34 includes a nose portion 104 that extends in a distal direction 106 the from distal end portion 48. One or all of the body portion 42, the through-passage 102, and the nose portion 104 may be concentric about the central axis 44. In some embodiments, the nose portion 104 as well as the side walls 52 of the spinal implant 34 may be configured as variously described at International Publication No. WO 2018/112324 to Abbasi, owned by the owner of the present application.

Embodiments depicting and describing additional details regarding the mounting and operation of the spinal implant 34 to the inserter 32 are presented below. The additional details may be implemented in the alternative and, in some cases, in combination, as will be evident to the skilled artisan in view of this disclosure.

Figure 3:
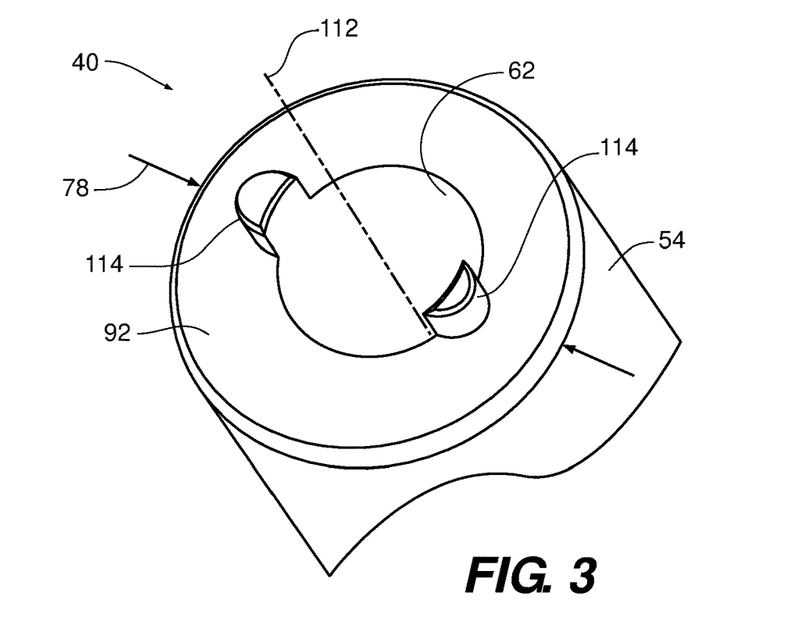
FIG. 3 is an enlarged, partial perspective view of a distal end of a shaft with rotational interlock protrusions for the spinal implant system of FIG. 1 according to an embodiment of the disclosure.
Figure 4:
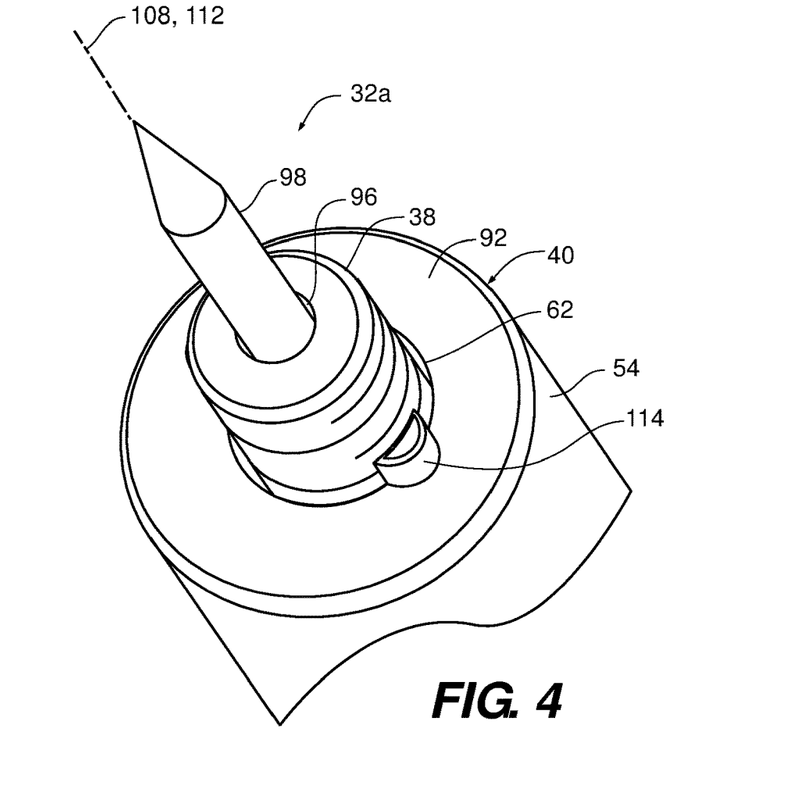
FIG. 4 is an enlarged, partial perspective view of an assembled inserter with the shaft of FIG. 3 according to an embodiment of the disclosure.

Referring to FIGS. 3 and 4, the distal end portion 54 of an inserter assembly 32a is depicted according to an embodiment of the disclosure. Herein, inserters 32 are referred to generically or collectively by reference character "32", and individually or specifically by reference character 32 followed by a letter suffix (e.g., "32a"). The inserter assembly 32a includes the shaft 40 with the inner retainer 38 extending therethrough. The inner retainer 38 may define the longitudinal passage 96 for passage of the guide wire 98 therethrough. The longitudinal passage 96 may be concentric with a rotation axis 108 of the spinal implant system 30, which may extend along a longitudinal centerline axis 112 of the inserter 32a. In some embodiments, distal end portion 54 of the shaft 40 includes at least one protrusion 114 that extends distally from the distal face 92 of the distal end portion 54. In some embodiments, the protrusion(s) 114 surrounds the central bore 62 (not depicted), and may define a polygonal shape (e.g., a square). The distal face 92 may be planar.

Figure 6:
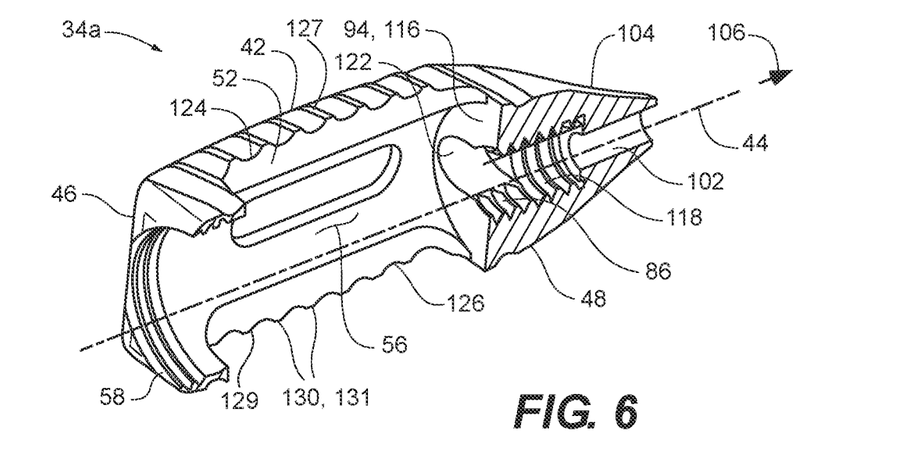
FIG. 6 is a perspective sectional view of the spinal implant of FIG. 5 according to an embodiment of the disclosure.

Referring to FIGS. 5 and 6, a spinal implant 34a configured for coupling with the inserter assembly 32a is depicted according to an embodiment of the disclosure. Herein, spinal implants 34 are referred to generically or collectively by reference character "34", and individually and specifically by reference character 34 followed by a letter suffix (e.g., "34a"). For the spinal implant 34a, the distal end portion 48 defines the mounting port 86 accessible from the proximal face 94 of the distal end portion 48. The mounting port 86 is configured to selectively attach directly to the inner retainer 38, for example by threaded connection (depicted).

In some embodiments, the proximal face 94 of the distal end portion 48 includes a registration surface 116 that surrounds the mounting port 86. The registration surface 116 may be planar and orthogonal to the central axis 44. For the spinal implant 34a, the registration surface 116 is proximal to the mounting port 86. The mounting port 86 may be tapped (as depicted) to define female threads 118 for threaded engagement with the inserter 32a. In some embodiments, distal end portion 48 defines at least one recess 122 accessible from the proximal face 94, the recess(es) 122 being configured to receive the protrusion(s) 114 of the inserter 32 during assembly. In some embodiments, the body portion 42 defines a superior opening 124 and an inferior opening 126, each defining a maximum length 123 and a maximum lateral dimension 125. The access port 58 is configured for selective attachment to the access tube 36, for example by threaded connection (depicted). In some embodiments, the access port 58 defines an inner diameter ID that enables passage of the maximum outer dimension 78 of the distal end portion 54 of the inserter 32*a*. In some embodiments, the access tube 36 as mounted to the access port 58 enables passage of the maximum outer dimension 78.

In assembly, when implementing the spinal implant 34*a*, the distal end portion 54 of the inserter 32*a* is inserted through the access port 58 into the receptacle 56 and rotationally aligned so that the protrusion(s) 114 is received by the recess(es) 122. The inserter 32*a* is attached to the distal end portion 48 of the spinal implant 34*a*, for example by mating the threaded distal end 64 of the inner retainer 38 of the inserter 32 with the female threads 118 of the mounting port 86, to secure the spinal implant 34 to the inserter 32 and to secure the protrusion(s) 114 within the recess(es) 122.

Each of the side walls 52 include superior edge surfaces 127 and inferior edge surfaces 129. In some embodiments, at least one of the superior edge surface 127 and the inferior edge surface 129 defines a plurality of gripping facets 130. Each of the plurality of gripping facets 130 may define a ridge line 131.

Functionally, the mating of the protrusion(s) 114 within the recess(es) 122 enables the spinal implant system 30 to impart rotational forces on the spinal implant 34*a* about the central axis 44 without excessively tightening or loosening the attachment 82. Accordingly, the mating of the protrusion(s) 114 within the recess(es) 122 provides a rotational interlock between the spinal implant 34*a* and the inserter 32*a* to enable rotation about the central axis 44. The interface 88 between the distal face 92 of the inserter 32*a* and the proximal face 94 of the distal end portion 48 of the spinal implant 34*a* also reduces stresses imparted at the attachment 82 (e.g., threads) between the inserter 32*a* and the spinal implant 34*a*, for example during tamping of the spinal implant system 30.

Figure 7:
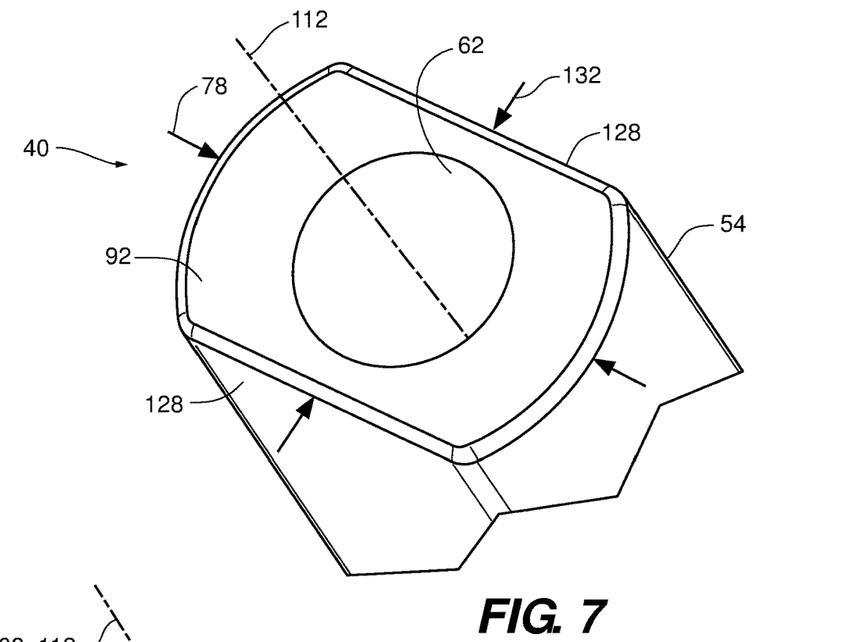
FIG. 7 is an enlarged, partial perspective view of a distal end of a shaft with a rotational interlocking cross-section for the spinal implant system of FIG. 1 according to an embodiment of the disclosure.
Figure 8:
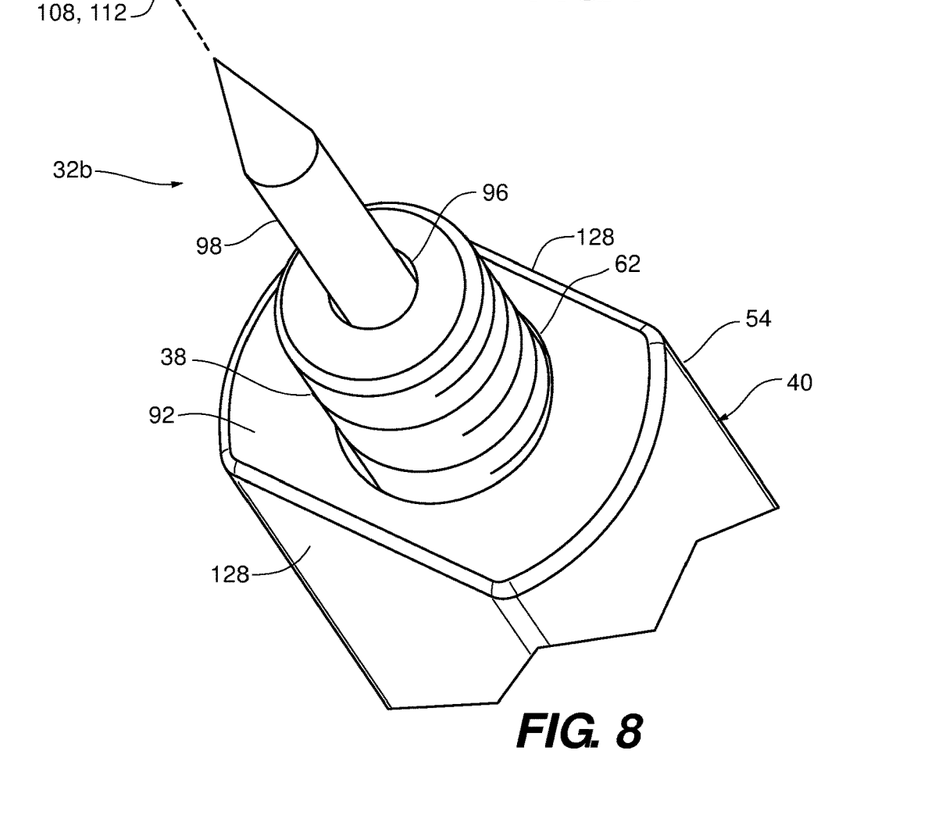
FIG. 8 is an enlarged, partial perspective view of an assembled inserter with the shaft of FIG. 7 according to an embodiment of the disclosure.

Referring to FIGS. 7 and 8, the distal end portion 54 of an inserter assembly 32*b* is depicted according to an embodiment of the disclosure. The inserter assembly 32*b* may include some of the same components and attributes as the inserter assembly 32*a*, which are indicated with same-labeled reference characters. The distal end portion 54 of the shaft 40 of the inserter assembly 32*b* includes diametrically opposed exterior flats 128 that defines a minimum outer dimension 132 extending orthogonal to the central bore 62 (i.e., parallel to the r direction of the r-O-z coordinate of FIG. 1).

Figure 9:
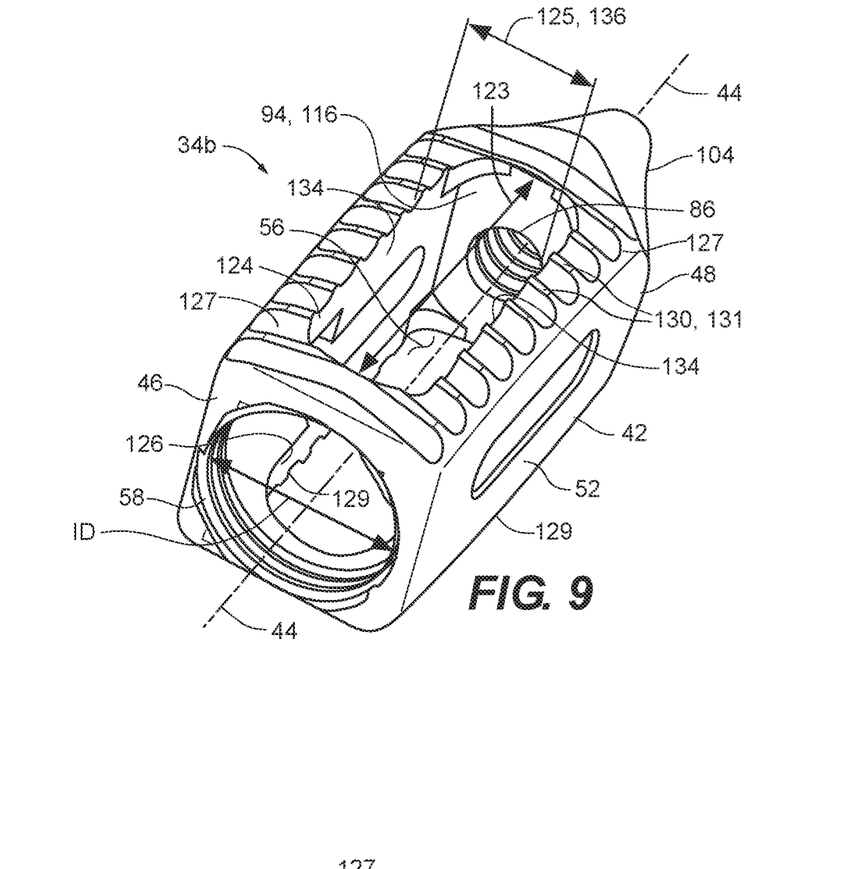
FIG. 9 is a perspective view of a spinal implant for use with the inserter of FIG. 8 according to an embodiment of the disclosure.
Figure 10:
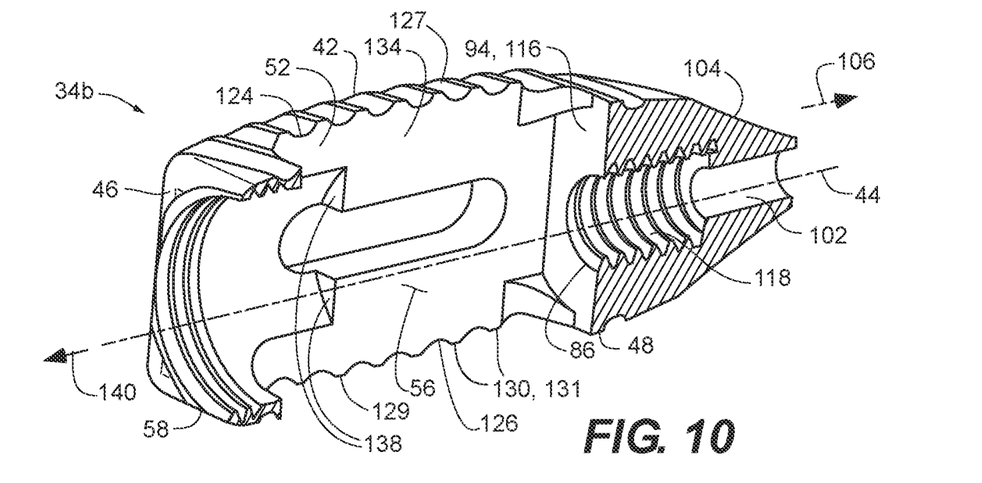
FIG. 10 is a perspective sectional view of the spinal implant of FIG. 9 according to an embodiment of the disclosure.

Referring to FIGS. 9 and 10, a spinal implant 34*b* configured for coupling with the inserter assembly 32*b* is depicted according to an embodiment of the disclosure. The spinal implant 34*b* may include some of the same components and attributes as the spinal implant 34*a*, which are indicated with same-labeled reference characters. The receptacle 56 of the spinal implant 34*b* includes opposed interior planar walls 134 spaced apart to define a lateral spacing 136 that enables sliding engagement with the exterior flats 128 of the shaft 40 of the inserter assembly 32*b*. In some embodiments, the interior planar walls 134 define an interior shoulder or shoulders 138 that face in a proximal direction 140. In some embodiments, the proximal face 94 of the distal end portion 48 includes a registration surface 116 that surrounds the mounting port 86. For the spinal implant 34*b*, the registration surface 116 is proximal to the mounting port 86.

Figures 11, 12:
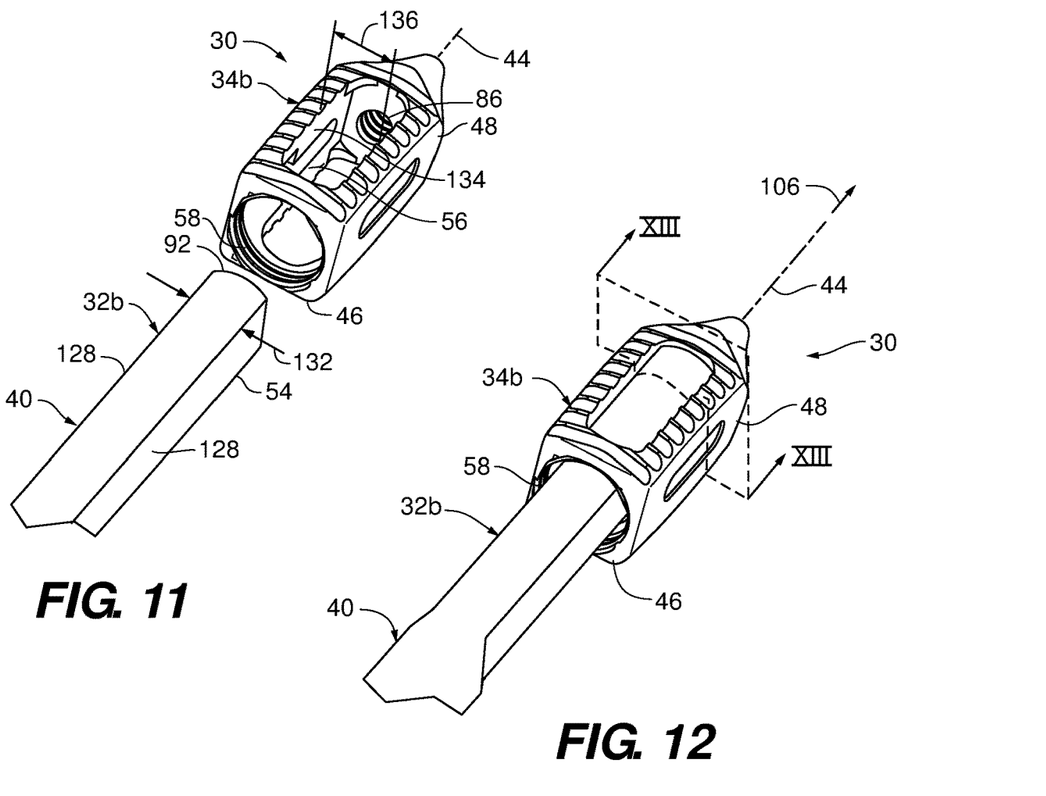
FIG. 11 is a partial perspective view of the shaft of FIG. 7 in rotational alignment for insertion into the spinal implant of FIG. 9 according to an embodiment of the disclosure.
FIG. 12 is a partial perspective view of the shaft of FIG. 7 inserted into the spinal implant of FIG. 9 according to an embodiment of the disclosure.
Figure 13:
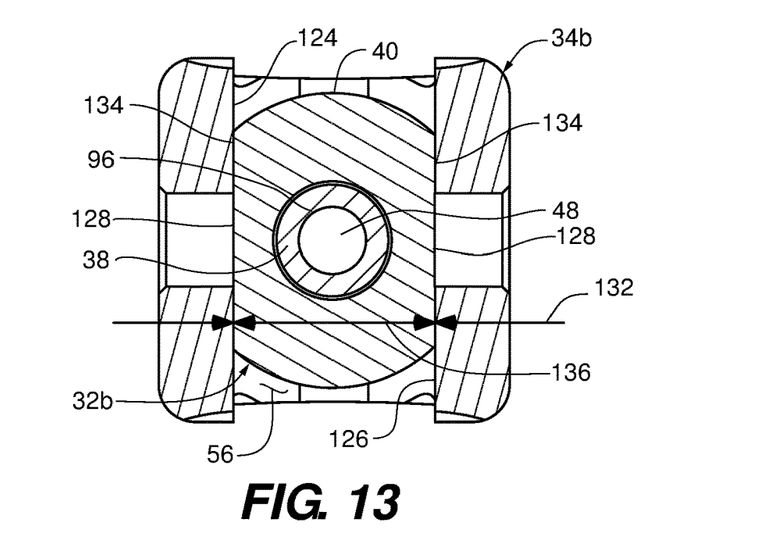
FIG. 13 is a sectional view at plane XIII-XIII of FIG. 12 according to an embodiment of the disclosure.

Referring to FIGS. 11 through 13, assembly of the spinal implant 34*b* to the inserter 32*b* is depicted according to an embodiment of the disclosure. In assembly, the minimum dimension 132 of the distal end portion 54 of the inserter 32*b* is rotationally aligned with the lateral spacing 136 of the receptacle of the 56 of the spinal implant 34*b* and the receptacle 56 slid over the distal end portion 54 of the shaft 40. The distal face 92 of the inserter 32*b* thereby passes through the access port 58, between the interior planar walls 134, and is brought into engagement with the distal end portion 48 of the spinal implant 34*b*. The inserter 32*b* and spinal implant 34*b* are secured to each other by attachment of the inner retainer 38 to the distal end portion 48 of the spinal implant 34*b*, for example by threaded engagement of the inner retainer 38 to the mounting port 86. The exterior flats 128 of the shaft 40 of the inserter 32*b* are thereby positioned adjacent to and in substantial contact with the interior planar walls 134 of the spinal implant 34*b*.

Functionally, the positioning of the exterior flats 128 adjacent the interior planar walls 134 within the receptacle 56 enables the inserter 32*b* to impart rotational forces on the spinal implant 34*b* about the central axis 44 without excessively tightening or loosening the attachment 82. The interface 88 between the distal face 92 of the inserter 32*b* and the proximal face 94 of the distal end portion 48 of the spinal implant 34*a* also reduces stresses imparted at the attachment 82 (e.g., threads) between the inserter 32*b* and the spinal implant 34*b*, for example during tamping of the spinal implant system 30. The interior shoulder(s) 138 may provide a registration surface for positioning a cannulated tool at a known location within the receptacle 56.

The complementary shape of the distal end portion 54 of the inserter 32*b* and the receptacle 56 of the spinal implant 34*b* thus provides a rotational interlock about the central axis 44. Other shapes besides the depicted opposed exterior flats 128 on an otherwise circular shaft may be utilized with similar effect. For example, the external surface of the distal end portion 54 of the inserter 32*b* may define a polygonal shape (e.g., square, rectangle, hexagon, octagon) with the receptacle configured to engage the polygonal shape in a rotationally interlocking manner. It is noted that any external shape that presents diametrically opposed external flats that are parallel to each other can be dimensioned to engage interior planar walls 134 of the spinal implant 34*b*. Alternatively, the receptacle 56 may be formed to define a void of the same shape as the distal end portion 54 of the inserter 32*b*. Other shapes contemplated for the rotational interlock include an oval, elliptical, or star (e.g. TORX®) shape.

Figures 14, 15:
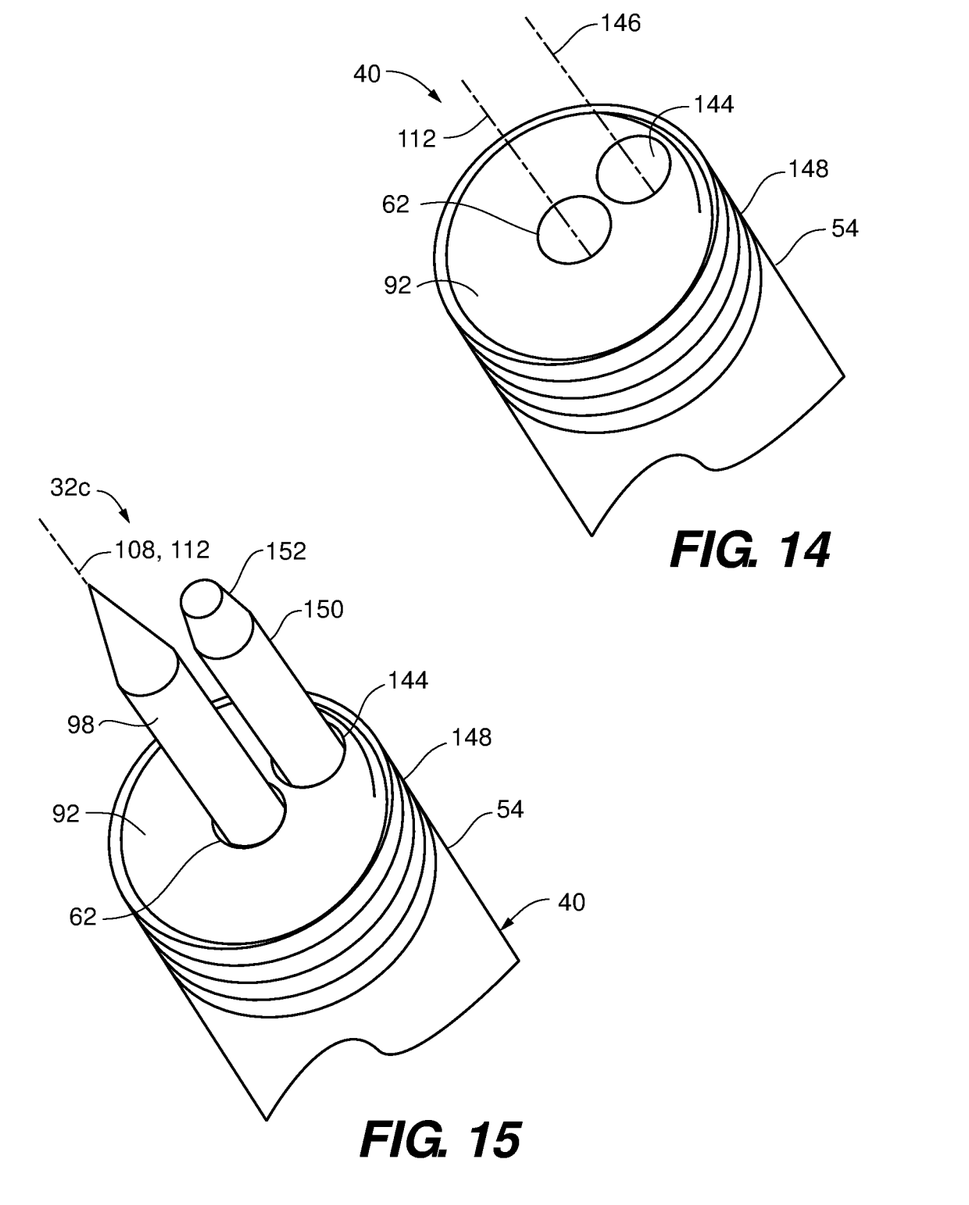
FIG. 14 is an enlarged, partial perspective view of a distal end of a shaft with a retractable lock pin for the spinal implant system of FIG. 1 according to an embodiment of the disclosure.
FIG. 15 is an enlarged, partial perspective view of an assembled inserter for the spinal implant system of FIG. 1 according to an embodiment of the disclosure.

Referring to FIGS. 14 and 15, the distal end portion 54 of an inserter assembly 32*c* is depicted according to an embodiment of the disclosure. The inserter assembly 32*c* may include some of the same components and attributes as the inserter assemblies 32*a* and 32*b*, which are indicated with same-numbered reference characters. The inserter 32*c* defines at least one eccentric passage 144 that defines a corresponding eccentric axis 146 that is parallel to the centerline axis 112 and is radially offset from the centerline axis 112. The distal end portion 54 of the shaft 40 of the inserter assembly 32*c* may include external threads 148. The inserter assembly 32*c* also includes a lock pin 150 configured to translate through any one of the at least one eccentric passage 144. The lock pin 150 may include a tapered lead-in surface 152 at a distal end 154.

Figure 16:
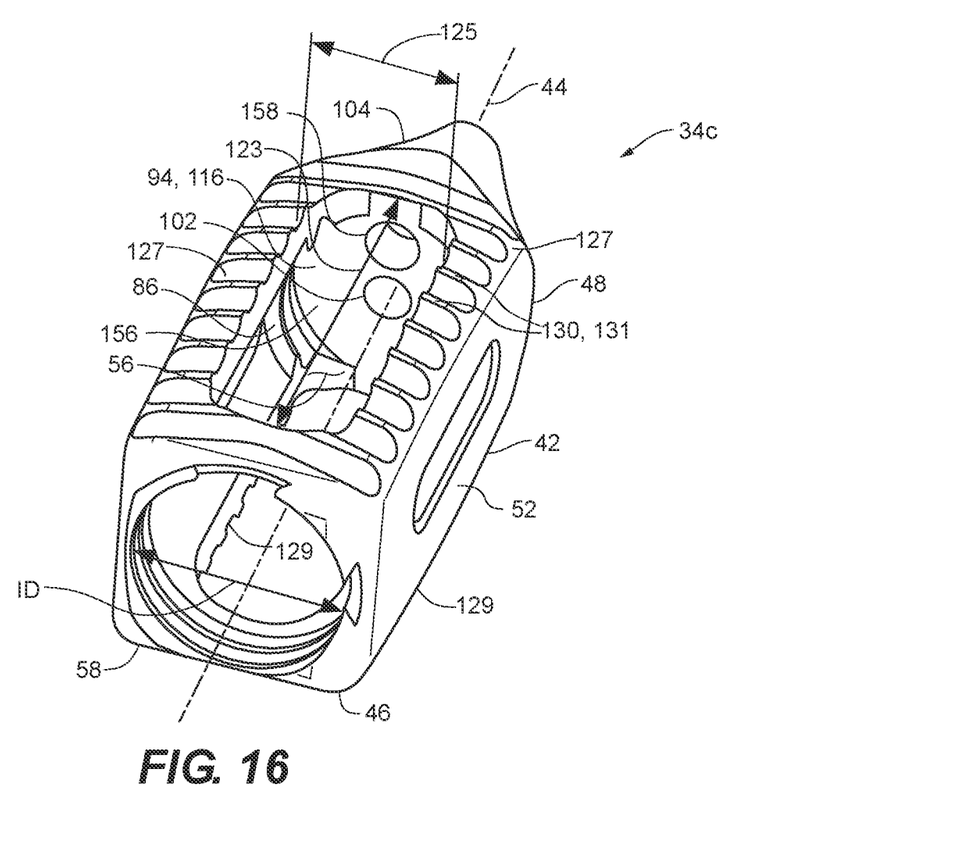
FIG. 16 is a perspective view of a spinal implant for use with the shaft of FIG. 15 according to an embodiment of the disclosure.
Figure 17:
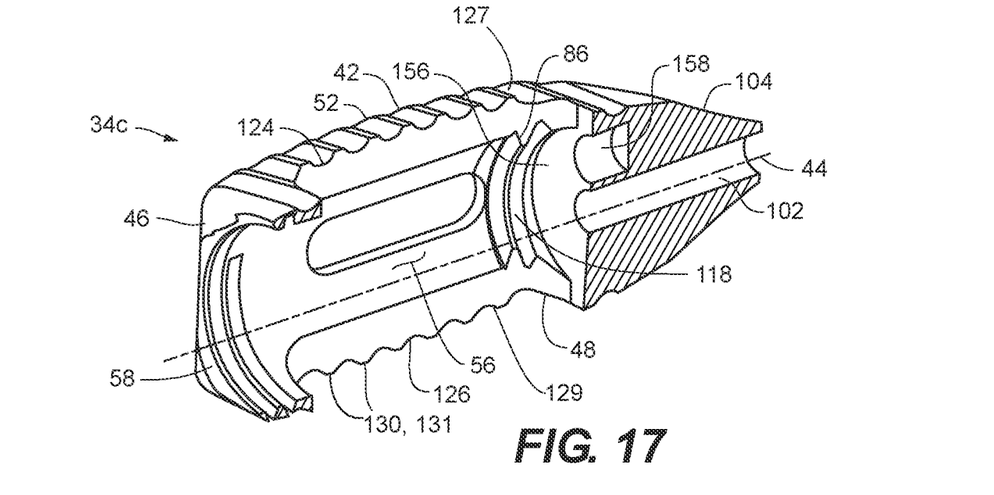
FIG. 17 is a perspective sectional view of the spinal implant of FIG. 16 according to an embodiment of the disclosure.

Referring to FIGS. 16 and 17, a spinal implant 34*c* configured for coupling with the inserter assembly 32*c* is depicted according to an embodiment of the disclosure. The spinal implant 34*c* may include some of the same components and attributes as the spinal implants 34a and 34b, which are indicated with same-labeled reference characters. Like the spinal implants 34a and 34b, the spinal implant 34c includes the registration surface 116, which may be planar and orthogonal to the central axis 44. Also, the mounting port 86 may be tapped (as depicted) to define the female threads 118 for threaded engagement with the inserter 32b.

However, unlike the spinal implants 34a and 34b, the registration surface 116 does not surround the mounting port 86; rather, the mounting port 86 surrounds the registration surface 116, with the registration surface 116 being distal to the mounting port 86. That is, the registration surface 116 is not disposed on a proximal face of the distal end portion 48 of the spinal implant 34c, but is at a distal face 156 of the mounting port 86, within the distal end portion 48 of the spinal implant 34c. The distal face 156 further defines a recess 158 for receiving the lock pin 150.

Figure 18:
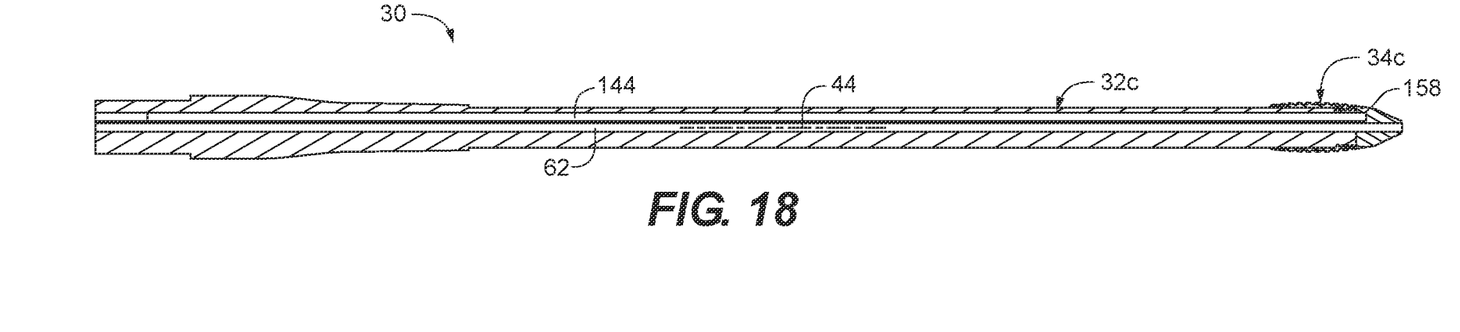
FIG. 18 is a sectional view of the shaft of FIG. 14 inserted into the spinal implant of FIG. 16.
Figure 19:
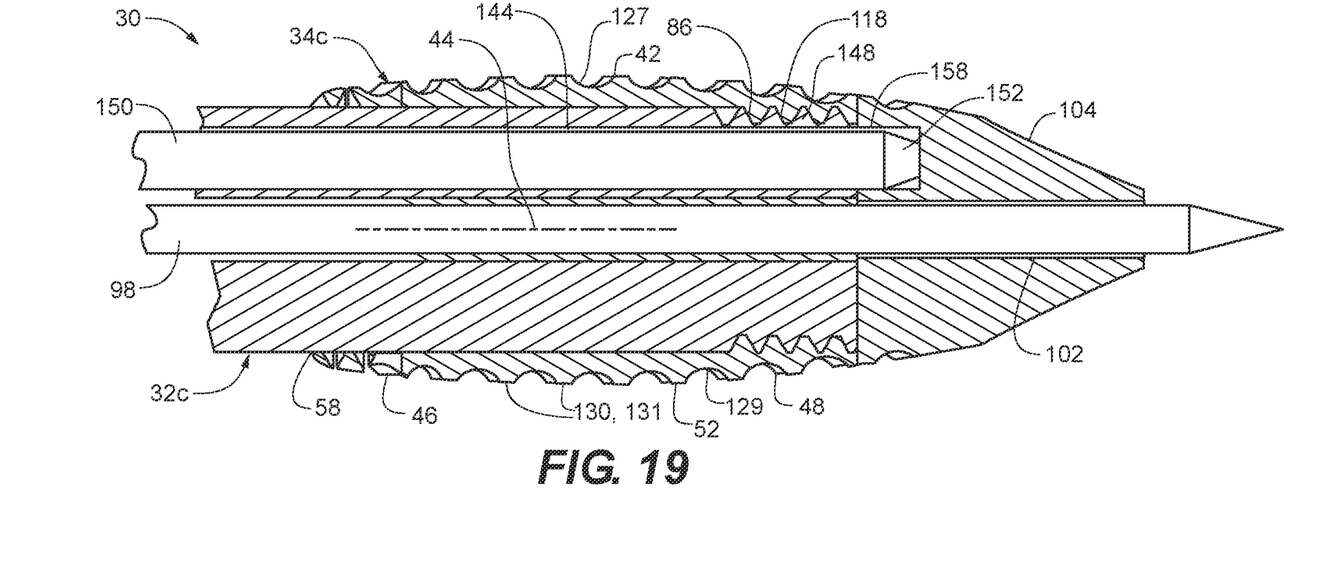
FIG. 19 is an enlarged, partial sectional view of the assembled inserter of FIG. 15 engaged with the spinal implant of FIG. 16.

Referring to FIGS. 18 and 19, assembly of the spinal implant 34c to the inserter 32b is depicted according to an embodiment of the disclosure. In assembly, the spinal implant 34c is slid over the distal end portion 54 of the shaft 40 of the inserter 32c, the distal end portion 54 thereby passing through access port 58 and engaging the mounting port 86. The distal end portion 42 of the shaft 40 is attached to the mounting port 86, for example by threaded engagement. In some embodiments, the distal face 92 of the inserter 32c is brought into contact with the registration surface 116 the spinal implant 34c. The lock pin 150 is inserted through one of the at least one eccentric passage 144 so that the distal end 154 is disposed within the recess 158.

Functionally, engagement of the lock pin 150 within the recess 158 enables the inserter 32c to impart rotational forces on the spinal implant 34c about the central axis 44 without excessively tightening or loosening the attachment 82. The interface 88 between the distal face 92 of the inserter 32c and the distal face 156 of the mounting port 86 also reduces stresses imparted at the attachment 82 (e.g., threads) between the inserter 32b and the spinal implant 34b, for example during tamping of the spinal implant system 30.

For the various embodiments of the disclosure, some or all of the components of the disclosed systems and devices are provided as a kit 160 (depicted at FIG. 1), complete with instructions 162 for use. The instructions 162 may include some or all of the steps described herein for assembly or operation (or both) of the spinal implant system 30. The instructions 162 are provided on a tangible, non-transitory medium, and may be physically included with the kit 160 such as on a printed document (depicted), compact disc, or flash drive. Non-limiting examples of a tangible, non-transitory medium include a paper document and computer-readable media including compact disc and magnetic storage devices (e.g., hard disk, flash drive, cartridge, floppy drive). The computer-readable media may be local or accessible over the internet. The instructions 160 may be complete on a single medium, or divided among two or more media. For example, some of the instructions 160 may be written on a paper document that instruct the user to access one or more of the steps of the method over the internet, the internet-accessible steps being stored on a computer-readable medium or media. The instructions 160 may embody the techniques and methods depicted or described herein using text, photos, videos, or a combination thereof to instruct and guide the user. The instructions may be in the form of written words, figures, photos, video presentations, or a combination thereof to instruct and guide the user.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

The disclosures of the following patent applications are hereby incorporated by reference herein in their entirety except for patent claims and express definitions contained therein: International Publication No. WO 2018/112324 to Abbasi; U.S. patent application Ser. No. 16/239,035 to Abbasi, filed Jan. 3, 2019; and U.S. patent application Ser. No. 16/839,167 to Abbasi et al., filed Apr. 3, 2020. Any incorporation by reference of documents above is limited such that no subject matter is incorporated that is contrary to the explicit disclosure herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. An implant for vertebral fusion, comprising:
a body portion defining a central axis that extends from a proximal end portion through a distal end portion of said body portion, said body portion defining an access port at said proximal end portion and a mounting port at said distal end portion, said mounting port being accessible from a proximal face of said distal end portion, said access port being configured for threadable engagement with an access tube and dimensioned for passage of an inserter therethrough, said mounting port being configured for selective attachment to said inserter,
wherein said body portion defines a superior opening and an inferior opening, each defining a maximum axial dimension and a maximum lateral dimension, said maximum axial dimension extending from proximate said proximal face of said distal end portion to proximate said access port, said body portion defining a clearance through passage of said maximum axial dimension and said maximum lateral dimension that extends through said superior opening, said body portion, and said inferior opening, and wherein said access port defines a minimum inner diameter that is greater than said maximum lateral dimension.

2. The implant of claim 1, wherein said proximal face of said distal end portion includes a planar registration surface that surrounds said mounting port, said planar registration surface being orthogonal to said central axis.

3. The implant of claim 1, wherein said distal end portion defines a through-passage that passes therethrough for passage of a guide wire.

4. The implant of claim 1, wherein said distal end portion includes a nose portion that extends in a distal direction from said distal end portion of said body portion.

5. The implant of claim 1, wherein said body portion, said access port, and said mounting port are concentric about said central axis.

6. The implant of claim 1, wherein said access port is dimensioned for passage of a portion of said inserter having a maximum outer dimension in a range of 5 millimeters to 15 millimeters inclusive.

7. The implant of claim 1, wherein said access port is dimensioned for passage of a portion of said inserter having a maximum outer dimension in a range of 5 millimeters to 9 millimeters inclusive.

8. The implant of claim 1, wherein said access port is dimensioned for passage of a portion of said inserter having a maximum outer dimension in a range of 6 millimeters to 8 millimeters inclusive.

9. The implant of claim 1, wherein a diameter of said access port is greater than a diameter of said mounting port.

10. The implant of claim 1, wherein said proximal end portion and said distal end portion are separated by opposed side walls that each include a superior edge surface and an inferior edge surface having gripping facets defined thereon.

11. A system for implanting a spinal implant, comprising:
a spinal implant including a body portion defining a central axis that extends from a proximal end portion through a distal end portion of said body portion, said body portion defining a superior opening and an inferior opening, each having a maximum axial dimension and a maximum lateral dimension, said maximum axial dimension extending from proximate said proximal face of said distal end portion to proximate said access port, said body portion defining a clearance through passage of said maximum axial dimension and said maximum lateral dimension that extends through said superior opening, said body portion, and said inferior opening, said body portion defining a threaded access port at said proximal end portion and a mounting port at said distal end portion, said mounting port being accessible from a proximal face of said distal end portion;

an access tube threaded for selective attachment to said threaded access port of said spinal implant; and an inserter configured to slide through said access tube and said access port and for selective attachment to said mounting port, wherein said access port defines a minimum inner diameter that is greater than said maximum lateral dimension.

12. The system of claim 11, wherein said inserter is an assembly that includes a shaft defining a central bore and an inner retainer translatable within said central bore.

13. The system of claim 12, wherein said inner retainer includes a threaded distal end for threadable connection with said mounting port.

14. The system of claim 11, wherein:
said access port includes first threads that mate with a distal end of said access tube for said selective attachment of said access tube to said access port; and
said mounting port includes second threads that mate with a distal end of said inserter for said selective attachment of said inserter to said mounting port.

15. The system of claim 14, wherein said proximal face of said distal end portion of said body portion includes a registration surface that surrounds said mounting port.

16. The system of claim 15, wherein, said registration surface is planar and orthogonal to said central axis and engages said distal face of said inserter when said inserter is selectively attached to said distal end of said spinal implant.

17. The system of claim 15, wherein:
said proximal face of said distal end portion of said body portion defines at least one recess; and
at least one protrusion extends beyond a distal face of said inserter and is received by a respective one of said at least one recess.

18. The system of claim 11, wherein said inserter includes a distal face that engages said distal end portion of said body portion when said inserter is selectively attached to said distal end of said spinal implant.

19. The implant of claim 11, wherein said proximal end portion and said distal end portion are separated by opposed side walls that each include a superior edge surface and an inferior edge surface having gripping facets defined thereon.

* * * * *